United States Patent [19]

Blunck et al.

[11] 4,023,930
[45] May 17, 1977

[54] METHOD AND APPARATUS FOR DETERMINING THE CONCENTRATION OF A GAS OR GASES IN A GAS MIXTURE BY SENSING THE COLORATION UNDERGONE BY REAGENT TEST PAPER, OR THE LIKE, IN RESPONSE TO EXPOSURE TO SUCH GAS OR GASES

[75] Inventors: Otto Blunck, Hamburg; Burkhart Seim, Ahrensburg; Karl-Heinz Retzow, Hamburg; Karl-Heinz Zorner, Norderstedt, all of Germany

[73] Assignee: Maihak AG, Hamburg, Germany

[22] Filed: Feb. 18, 1975

[21] Appl. No.: 550,646

[30] Foreign Application Priority Data

Feb. 15, 1974 Germany .......................... 2407224

[52] U.S. Cl. ........................ 23/232 R; 23/232 E; 23/253 TP; 23/254 E; 23/255 E
[51] Int. Cl.$^2$ ........................................ G01N 31/22
[58] Field of Search ......... 23/232 R, 232 E, 254 R, 23/254 E, 255 R, 255 E, 253 TP

[56] References Cited

UNITED STATES PATENTS

| | | | |
|---|---|---|---|
| 2,554,414 | 5/1951 | McClendon | 23/255 R |
| 2,602,729 | 7/1952 | Curry | 23/255 R |
| 2,622,015 | 12/1952 | Cooper et al. | 23/255 R |
| 2,800,397 | 7/1957 | Offutt et al. | 23/232 R |
| 2,895,807 | 7/1959 | Sorg et al. | 23/232 R X |

Primary Examiner—Norman Yudkoff
Assistant Examiner—Barry I. Hollander
Attorney, Agent, or Firm—Michael J. Striker

[57] ABSTRACT

The concentration of gas is determined by monitoring the coloration of a reagent test paper, or the like, whose color changes progressively or otherwise in response to continued exposure to such gas. The concentration is determined by determining the length of time which the reagent test paper must be exposed to the gas for the coloration of the test paper to reach a preselected threshold value.

8 Claims, 2 Drawing Figures

METHOD AND APPARATUS FOR DETERMINING THE CONCENTRATION OF A GAS OR GASES IN A GAS MIXTURE BY SENSING THE COLORATION UNDERGONE BY REAGENT TEST PAPER, OR THE LIKE, IN RESPONSE TO EXPOSURE TO SUCH GAS OR GASES

BACKGROUND OF THE INVENTION

The invention relates to a method and an apparatus for determining the concentration of a gas or a gas component in a gas mixture, by means of the coloration of a reagent test paper.

A variety of measuring devices are known which make use of elongated strips of reagent test paper as the measuring means. In consequence of their simple construction they are very reliable. On account of the extreme measuring sensitivity, they guarantee the accurate determination of for example smoke concentrations or the analysis of gases of such low concentration that measurement by other devices and other methods could be performed only at great expense.

A further use of the known apparatuses is for example the monitoring of a gaseous atmosphere where only the exceeding of a predetermined, for example dangerous, threshold value is to be signalled; so long as the concentration remains below this preselected value, there is no need for an indication, since only the distinction "beneath or above the threshold value" is of interest.

For these and other purposes, the conventional test paper measuring devices have the disadvantage that they continually, i.e., even in "normal conditions", when the gas concentration is beneath the threshold value, steadily consume test paper. These devices operate with continual test paper advancement, either continuously, for example at 1 millimeter per minute, or discontinuously, for example at the rate of one exposure field per gas exposure, i.e., independently of the indicated gas concentration. The result is a considerable consumption of reagent test paper and accordingly considerable operating expense.

SUMMARY OF THE INVENTION

It is a general object of the invention to provide a method and an apparatus which overcomes the afore-described disadvantages.

This object, and others which will become more understandable from the following description of specific embodiments, can be met, according to one advantageous concept of the invention, by an inventive method characterized in that the concentration of the gas or gas components(s) of interest is determined indirectly by determining the time required for the gas-sensitive test paper to undergo coloration to a predetermined extent.

According to one advantageous concept of the invention, the time interval required for the test paper coloration to advance to a preselected threshold value is compared with a preselected reference time interval.

An alarm is generated when the time interval required for coloration to advance to the threshold value is less than the preselected reference time interval, indicating a gas concentration higher than that corresponding to the preselected reference time interval.

The reference time interval is preselected in dependence upon the gas components to be detected and their concentrations.

The test paper is advanced—i.e., new test paper is exposed to the gas to be monitored—only when the coloration of the previously exposed test paper has advanced to the preselected threshold value.

With the inventive method use can be made, inter alia, of a reagent test paper which is responsive to acidic gas components.

The invention also comprehends an apparatus for performing the inventive method. The apparatus advantageously includes a measuring chamber and a comparison chamber with a light source and light detectors arranged in a bridge circuit, with indicating means and means for transporting reagent test paper and exposing it to the gas to be monitored, characterized in that the light difference current measuring means is connected to the drive means for the paper transporter by means of a threshold detecting circuit, the latter being connected to an alarm device through the intermediary of at least one timer.

According to an advantageous concept of the invention, the threshold detecting circuit, such as a Schmitt trigger, is connected via timers to a plurality of alarm generators.

The inventive apparatus advantageously compares the time interval required for the test paper coloration to advance to the preselected threshold value against the preselected time interval or intervals set on one or more timers, and generates an alarm when the time interval elapsing before attainment of the coloration threshold is shorter than the time intervals set on one or more of the timers. Preferably, the time intervals preset on the timers are adjustable. An important application of this inventive concept is to apparatus of the type in question using reagent test paper which is sensitively responsive to all acidic gas components.

The novel features which are considered as characteristic for the invention are set forth in particular in the appended claims. The invention itself, however, both as to its construction and its method of operation together with additional objects and advantages, will be best understood from the following description of specific embodiments when read in connection with the accompanying drawing.

DESCRIPTION OF THE PREFFERED EMBODIMENTS

Figure 1:
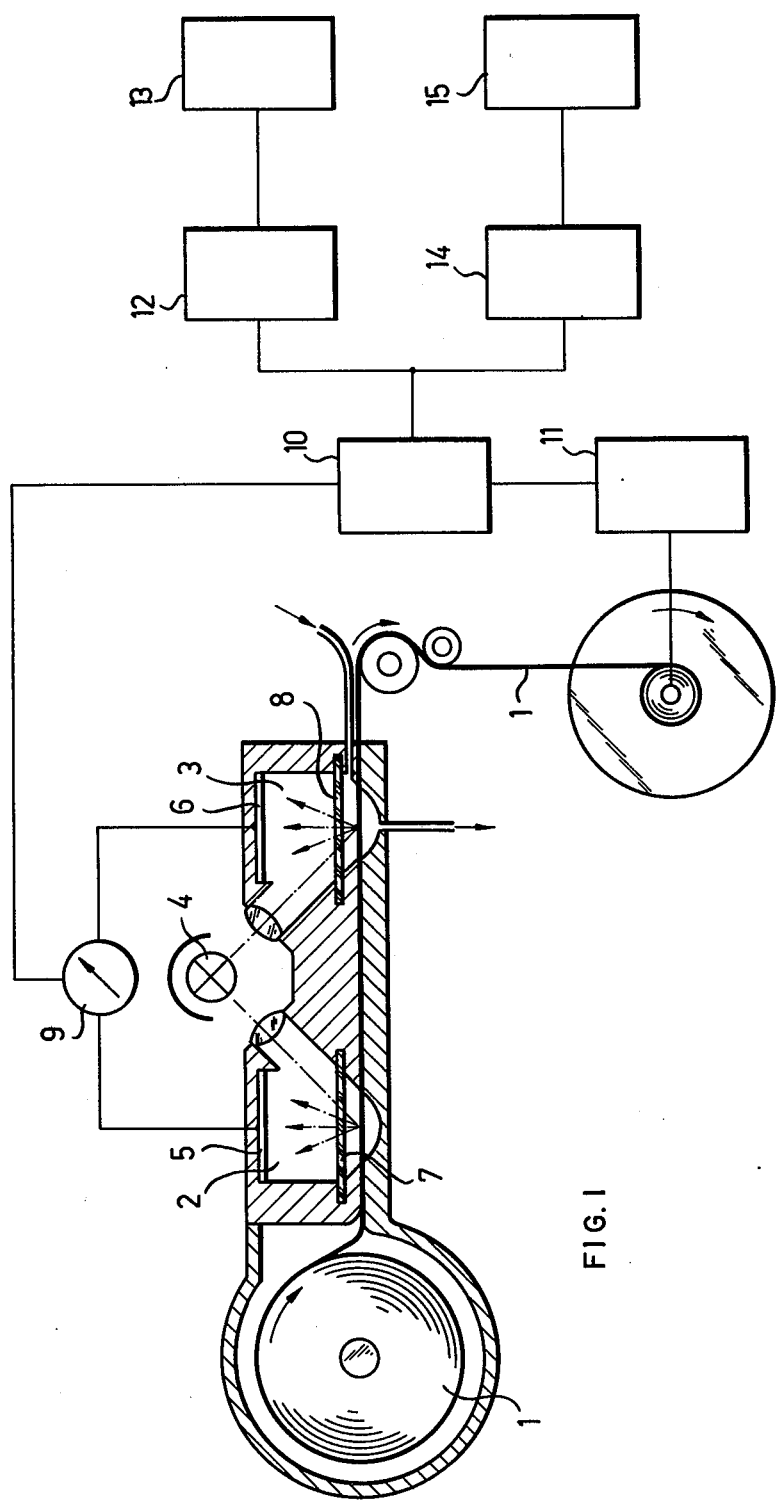
FIG. 1 schematically depicts one embodiment of an inventive apparatus for performing the inventive method, together with the control signal therefor.

A relatively narrow test paper band 1, which reacts to the gas components to be measured by undergoing a change of color to a greater or lesser degree indicative of the concentration of the gas components, passes first through a comparison chamber 2 and then through a measuring chamber 3. The comparison chamber 2 contains air; the measuring chamber 3 is supplied with the gas to be measured.

The test paper 1 in both chambers 2, 3 is exposed to light from a common light source 4 through respective windows 7, 8. The light radiation diffusely reflected from the paper 1 is sensed by two photoelectric elements 5, 6. The photoelectric element 5 senses the light reflected from the test paper when the test paper is in the comparison chamber 2 and not exposed to the gas to be measured. The photoelectric element 6 senses the light reflected from the test paper when the test paper is in the measuring chamber 3 and more or less colored as a result of reaction with the gas component or components to be measured. The current difference resulting from these two detections is proportional to the content in the test gas of the gas components to be monitored multiplied by the duration of the exposure of the paper in test chamber 3 to the gas. This current difference is measured using the light-difference current measuring device 9.

For example, the photoelectric elements 5, 6 could be photovoltaic cells connected to the input of a difference amplifier, schematically indicated by symbol 9, the output of which furnishes an electrical voltage proportional to the difference in detected coloration of the test paper in the two chambers 2, 3. Depending upon the initial and final colors of the test paper undergoing coloration, color filters of suitable color can be provided in front of the photosensitive surfaces of the photoelements 5, 6. For example, if the test paper undergoes a change of color from red to blue, it would be appropriate to position blue color filters in front of the photosensitive surfaces of the photoelements 5, 6.

Reference numeral 10 designates a threshold circuit, such as a Schmitt trigger, which is preset to a threshold value appropriate for the intended application. When the threshold value is reached, the drive 11 for the paper band is turned on, and the paper band 1 is advanced by a distance equal to one field. The new field now begins to color, if the gas components in question are present. The time required for the coloring of the test paper to advance to an extent resulting in exceeding of the preselected threshold value, is measured. This time is compared with a preselected time interval, set on a first time-limiting relay 12, this preselected time interval being selected in accordance with the intended use of the illustrated apparatus. If the threshold time is lower than the preselected time set on the time-limiting relay 12 (e.g., 3 to 30 seconds) then the alarm unit 13 generates an alarm signal. Evaluating the rapidity of the indication as the measured value prevents aging of the paper and leakage-produced colorations of the paper from gradually leading to a false alarm signal. The paper is normally—i.e., in the case of concentrations beneath the threshold value—not further transported; if the threshold value is reached, then a new field is advanced into the test chamber 3, and the quickness of the now following coloration is a measurement for the concentration of the gas components to be measured. In this way, although the arrangement is always in readiness to generate an alarm signal, the consumption of test paper is held to a minimum, and economical operation becomes possible.

Another advantage of the illustrated arrangement is that the use of a comparison chamber 2 substantially identical to the measuring chamber 3 compensates for the effects of aging and leakage of gases into the storage compartment of the unused test paper 1. For example, the test paper, because of aging or because of sensitivity to ambient gases which leak into the storage compartment for the unused test paper, may undergo a significant amount of coloration before advancing into the measuring chamber 3. This precoloration, which is not actually indicative of the coloration occurring in measuring chamber 3, is detected by photoelement 5, and the corresponding signal (current or voltage) is substracted from the signal generated by photoelement 6. In this way, th pre-coloration can be very effectively caused to have no effect in the measurement.

An additional advantage is that the threshold value time, in addition, is to be compared with the delay time of a second (or further) time-limiting relay 14. The delay time of this second time-limiting relay 14, which likewise is selected in accordance with the intended use of the apparatus, is preferably larger (e.g., 20 to 240 seconds) than the time delay of the first time-limiting relay 12, but shorter than the coloring time constant associated with paper aging and leakages. In this way, there are established two measuring ranges for the measuring device; further measuring ranges can be established by employing additional time-limiting relays.

Test paper measuring devices, as is known, react very sensitively to the gas components to be measured; they accordingly make possible the measurement of very small gas concentrations, for example in the parts-per-billion range. As a result, the inventive apparatus can be used in many important applications involving such ranges. It has been shown that the electrical and electronic components, which for example can be grouped into relatively large packages in the form of integrated circuits and the like, in the event of dangerous temperature increases, such as result from short circuits, send out from their casings or sheaths (e.g., cable sheaths) acidic components, before they actually go aflame. The acidic components, predominantly HCl, can be monitored with the inventive apparatus if use is made of a special indicator paper. The first time-limiting relay 12 with the shorter time delay supplies the alarm signal generator 13 a signal, when such marked heatings-up occur as to require immediate countermeasures, such as shut-off of the entire apparatus or other equipment which is to be protected. With the aid of the second time-limiting relay 14 with the longer time delay, and an alarm signal generator 15 connected thereto, it is possible to detect and indicate such temperature rises which do not spell immediate danger, but which will result in damage to the electronic components after the passage of sufficient time. Accordingly, there is provided an indication at an early stage of the need for preventive measures.

All in all, with the invention, one is provided with a measuring apparatus which at an early time signals a possible danger of fire, so that fire-prevention measures can be initiated before any considerable damage can occur.

It will be understood that the time-limiting relays 12, 14 are resettable devices. When the drive 11 for the paper transport is activated, and effects paper advancement by one field (e.g., the length of the measuring chamber 3 or alternatively the length occupied by the chambers 2,3 plus the intermediate space), the time-limiting relays 12, 14 automaticaly become reset.

Instead of resettable time-limiting relays, use could be made of a completely electronic circuit arrangement. The light-sensitive elements 5, 6, as mentioned before, could be photovoltaic cells connected to the two inputs of a difference amplifier 9 operative for generating an electrical signal indicative of the difference in coloration between the test paper in the chamber 2 and the test paper in the chamber 3. The threshold circuit 10 could consist of a conventional Schmitt trigger whose input constitutes the input of the circuit 10. Also forming part of circuit 10, and connected to the output of the Schmitt trigger could be a differentiator, which would convert the "0" to "1" and "1" to "0" transitions of the Schmitt-trigger output signal into pulses. Connected to the output of the differentiator would be a half-wave rectifier which passes only the first of the two pulses generated by the differentiator, namely the pulse corresponding to the detection of the coloration having reached the threshold extent. The output of the half-wave rectifier would constitute the output of the threshold circuit 10. The circuit 11 could be comprised essentially of a monostable circuit the output of which controls the conductivity of an electronic switch connected in the current path of the drive motor for the paper transport. The monostable circuit, when triggered by a pulse appearing at the output of circuit 10, would energize the drive motor for a time interval, preset on the monostable circuit, and corresponding to the time required for advancement of the paper by a distance equal to one field. The timing device 12 could be comprised of a monostable circuit and an AND-gate. One input of the AND-gate would be connected to the output of this monostable circuit and the other input of the AND-gate would be connected to the output of the half-wave rectifier in circuit 10. The input of the monostable circuit in circuit 12 would likewise be connected to the output of the half-wave rectifier in circuit 10. When circuit 10 generates the threshold-indicating pulse, this pulse triggers the monostable circuit in circuit 12, thereby enabling the AND-gate in circuit 12 for a corresponding time period. The output of such AND-gate would be connected to the alarm device 13, for example to a self-locking relay, or the transistorized equivalent, connected in the current path of a buzzer or warning light. The circuitry for components 14 and 15 would be the same as that for components 12 and 13, but the monostable circuit in circuit 14 would have a different unstable time interval.

Figure 2:
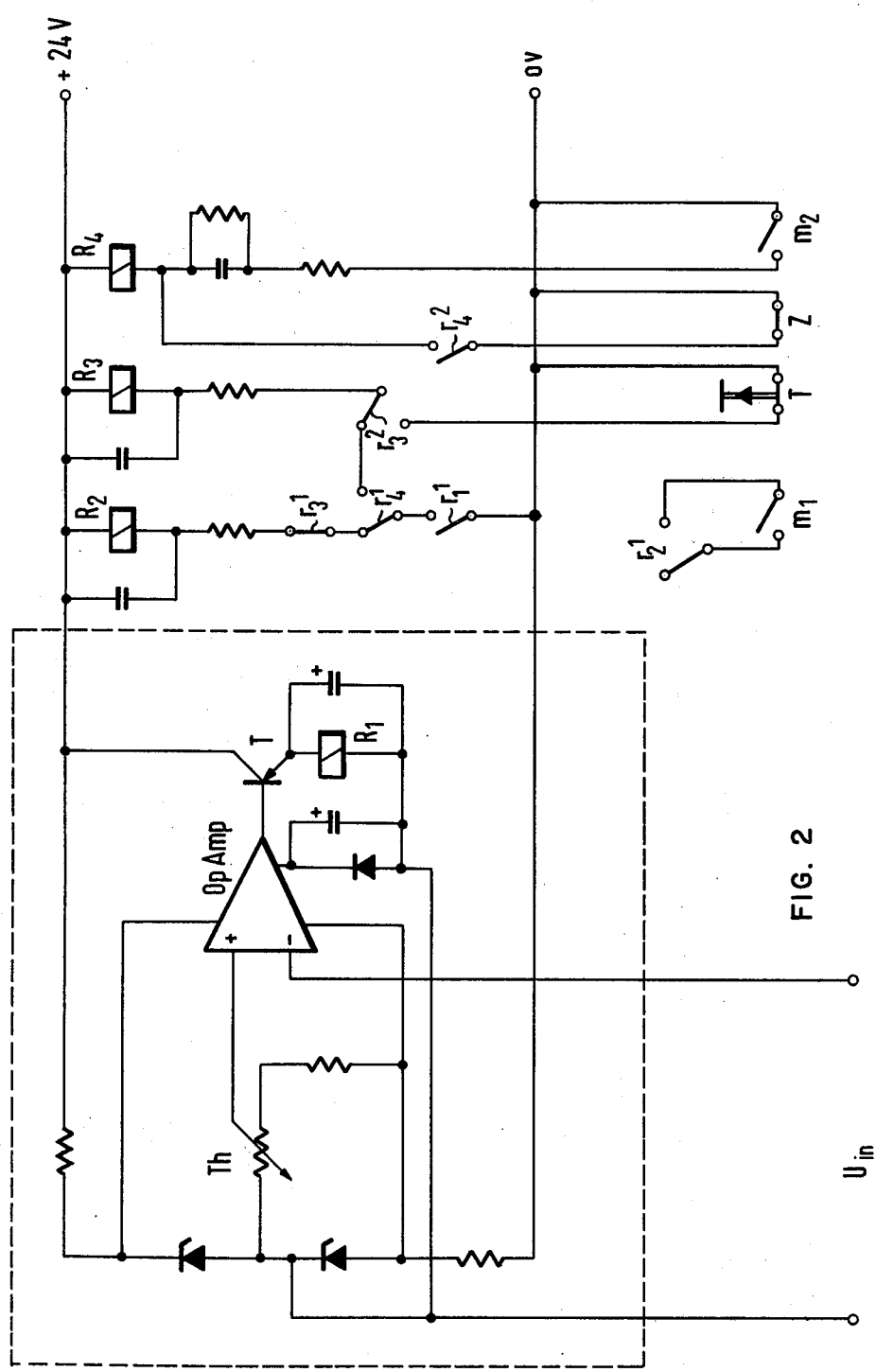
FIG. 2 depicts details of the control circuit.

FIG. 2 depicts details of the control circuit shown in FIG. 1. The circuit shown in the brokenline box corresponds to the threshold switch 10 of FIG. 1. This threshold switch is basically a voltage comparator and is essentially comprised of a potentiometer Th, an operational amplifier Op Amp and a switching transistor T. The threshold value is selected using potentiometer Th. If the magnitude of the input signal $U_{in}$, corresponding to the extent of coloration of the test paper, exceeds the selected threshold value, then transistor T becomes conductive, thereby energizing relay winding $R_1$. The associated normally open relay switch $r_1^1$ closes, and motor relay winding $R_2$ via relay switch $r_1^1$ and normally closed relay switch $r_4^1$ becomes energized. The motor starts to run, and a camshaft switch $m_1$ connected with the drive bridges relay switch $r_2^1$; accordingly, the motor can continue to run even after the deenergization of the relay winding $R_2$, until such time as a fresh section of test paper has moved into position beneath the scanning means. If the transport comes to a standstill, motor contact $m_2$ energizes relay winding $R_4$ by a surge, and thereafter the energization of relay winding $R_4$ is maintained by means of self-locking relay switch $r_4^2$.

Simultaneously, the timer Z is started and the alarm relay winding $R_3$ connected with the threshold switch via relay switch $r_4^1$. If the coloration-indicating signal applied to the threshold circuit exceeds the selected threshold value within the selected time, then alarm relay winding $R_3$ becomes energized via $r_1^1$. Once relay winding $R_3$ becomes energized its associated self-locking switch $r_3^2$ holds it energized until the current path for relay winding $R_3$ is interrupted by means of interrupter switch T.

If no alarm signal is generated within the selected time, the relay winding $R_4$ becomes deenergized by means of the timer switch Z. The timer automatically resets itself and the motor relay winding $R_2$ becomes connected once more to the threshold circuit via contact $r_4^1$.

The process and apparatus are designed for the detection of HCl gas, which is formed during PVC cable fires. For the purpose of providing the requisite indication, the test paper is soaked in a 1% solution of Congo Red. The red test paper changes color to blue when exposed to hydrogen chloride.

It will be understood that each of the elements described above, or two or more together, may also find a useful application in other types of constructions and circuits differing from the types described above.

While the invention has been illustrated and described as embodied in a gas-concentration measuring apparatus and method using an elongated strip of test paper, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore such adaptations should and are intended to be comprehended within the meaning and range of equivalence of the following claims.

What is claimed as new and desired to be protected by Letters Patent is set forth in the appended claims:

1. A method of determining the concentration of a gas by monitoring the coloration of a reagent test paper whose color changes progressively in response to continued exposure to such gas, comprising the steps of determining the length of time which such reagent test paper must be exposed to such gas for the coloration of the test paper to reach a preselected threshold value, comparing the length of time which is required for the coloration to reach said preselected threshold value against a preselected reference time, and exposing fresh test paper to the gas mixture only when the coloration of the previously exposed test paper has reached said preselected threshold value.

2. A method as defined in claim 1, wherein said preselected reference time is selected in dependence upon the composition of the gas to be measured and the concentration thereof.

3. A method as defined in claim 1, wherein said determining step comprises using a test paper which responds to acidic gas components.

4. A method as defined in claim 1, further including the steps of detecting when the length of time which is required for the coloration to reach said preselected threshold value is shorter than the preselected reference time and in response to such detection generating an alarm signal.

5. An apparatus for determining the concentration of a gas or gases, comprising, in combination, means defining a measuring chamber; means for transporting test paper into said chamber; light source means for illuminating the test paper in said chamber; means for introducing into said chamber the gas or gases whose concentration is to be measured; light-detecting means operative for generating a signal indicative of the extent to which test paper in said measuring chamber undergoes coloration in response to exposure to the gas or gases; and means for generating an alarm signal when the time interval elapsing between introduction of fresh test paper into said chamber and the assumption by said signal of a preselected threshold value is less than a preselected time interval, including means for effecting transport of fresh test paper into said chamber in response to assumption by said signal of said preselected threshold value when the time interval elapsing between the previous introduction of fresh paper into said measuring chamber and the assumption by said signal of said preselected threshold value is longer than said preselected time interval.

6. An apparatus as defined in claim 5, further including means defining a comparison chamber, and wherein said means for transporting fresh test paper into said measuring chamber is additionally operative for transporting fresh test paper into said comparison chamber, wherein said light source means is additionally operative for illuminating the test paper in said comparison chamber, wherein said light-detecting means comprises means for sensing the coloration of test paper in said comparison chamber and generating a corresponding first signal and means for sensing the coloration of test paper in said measuring chamber and generating a corresponding second signal and means for determining the difference of said first and second signals and deriving therefrom said signal indicative of the extent to which test paper in said measuring chamber undergoes coloration in response to exposure to the gas or gases therein, whereby the lastmentioned signal is kept free of the effect of pre-coloration of test paper occurring not in response to exposure to the gas or gases in the measuring chamber but as a result of test paper aging, unintentional exposure to activating gases, and the like.

7. An apparatus as defined in claim 5, wherein said means for generating an alarm comprises threshold detecting means connected to the output of said light-detecting means for receipt of said signal and operative for generating an output signal when said signal assumes said preselected threshold value, and a plurality of timing means connected to the output of said threshold detecting means and respectively operative for generating an alarm when the time interval elapsing between introduction of fresh paper into said chamber and the assumption by said signal of a preselected threshold value is less than any one of a plurality of preselected time intervals respectively associated with said plurality of timing means.

8. An apparatus as defined in claim 5, including means operative when the time interval elapsing between introduction of fresh test paper into said chamber and the assumption by said signal of the preselected threshold value is less than the preselected time interval for automatically causing fresh test paper to be transported into said measuring chamber.

* * * * *